US008302776B2

(12) United States Patent
Lien

(10) Patent No.: US 8,302,776 B2
(45) Date of Patent: Nov. 6, 2012

(54) PACK OF ORAL CARE ITEMS

(75) Inventor: Khoa T. Lien, Milton, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 169 days.

(21) Appl. No.: 12/649,730

(22) Filed: Dec. 30, 2009

(65) Prior Publication Data

US 2011/0155628 A1 Jun. 30, 2011

(51) Int. Cl.
 *B65D 61/00* (2006.01)
(52) U.S. Cl. ............. 206/581; 206/370; 383/37; 383/38
(58) Field of Classification Search ............. 383/37–40, 383/207–209; 206/484, 581, 361
 See application file for complete search history.

(56) References Cited

U.S. PATENT DOCUMENTS

| | | | | |
|---|---|---|---|---|
| 3,456,866 A * | 7/1969 | Civitello | ............. | 383/40 |
| 3,608,566 A * | 9/1971 | Storandt | ............. | 132/312 |
| 4,660,721 A * | 4/1987 | Mykleby | ............. | 206/439 |
| 5,098,297 A | 3/1992 | Chari et al. | | |
| 5,222,600 A * | 6/1993 | Stoddard et al. | ............. | 206/370 |
| 5,378,226 A | 1/1995 | Hanifl et al. | | |
| 5,704,906 A | 1/1998 | Fox | | |
| 5,709,866 A * | 1/1998 | Booras et al. | ............. | 424/400 |
| 6,068,476 A | 5/2000 | Point | | |
| 6,082,585 A * | 7/2000 | Mader et al. | ............. | 222/83 |
| 6,234,675 B1 * | 5/2001 | Saad et al. | ............. | 383/38 |
| 6,387,068 B1 | 5/2002 | Naughton | | |
| 6,811,339 B1 | 11/2004 | Tsaur | | |
| 7,815,050 B2 * | 10/2010 | Martin et al. | ............. | 206/542 |
| 2002/0044816 A1 | 4/2002 | Strauss | | |
| 2004/0138611 A1 | 7/2004 | Griffiths et al. | | |
| 2004/0186183 A1 | 9/2004 | Johnson | | |
| 2005/0269219 A1 | 12/2005 | Discko | | |
| 2006/0228158 A1 | 10/2006 | Levine et al. | | |
| 2006/0283728 A1 | 12/2006 | Patrick et al. | | |
| 2007/0189639 A1 * | 8/2007 | Revness | ............. | 383/37 |

FOREIGN PATENT DOCUMENTS

| | | |
|---|---|---|
| WO | WO 2009/085636 A1 | 7/2009 |
| WO | WO 2009/132052 A2 | 10/2009 |

* cited by examiner

*Primary Examiner* — J. Gregory Pickett
*Assistant Examiner* — Raven Collins
(74) *Attorney, Agent, or Firm* — Karl V. Sidor

(57) ABSTRACT

A pack of oral care items that allows for simultaneous opening and easy access to the items contained in the pack. The pack of oral care items includes two or more flexible packages. The flexible packages may be arranged in parallel. One flexible package may be an inner package that is located substantially within another flexible package that forms an outer package. The inner package may include an integral burst pouch configured to release a liquid into an interior space of the outer package while keeping the interior space of the inner package dry. Each flexible package includes a frangible region located at or adjacent a top portion and at least one oral care item is disposed within an interior space of each flexible package. At least one fastening means joins the flexible packages together into a substantially unitary pack so the frangible regions are juxtaposed and the top portions of the packages are aligned to allow for opening simultaneously by applying a force to the frangible regions to open the flexible packages. Upon opening of the top portions of the flexible packages, the central portions of the flexible packages are configured for axial movement simultaneously toward the bottom portions to expose at least the tops of the oral care items so they can be readily grasped by a user.

16 Claims, 4 Drawing Sheets

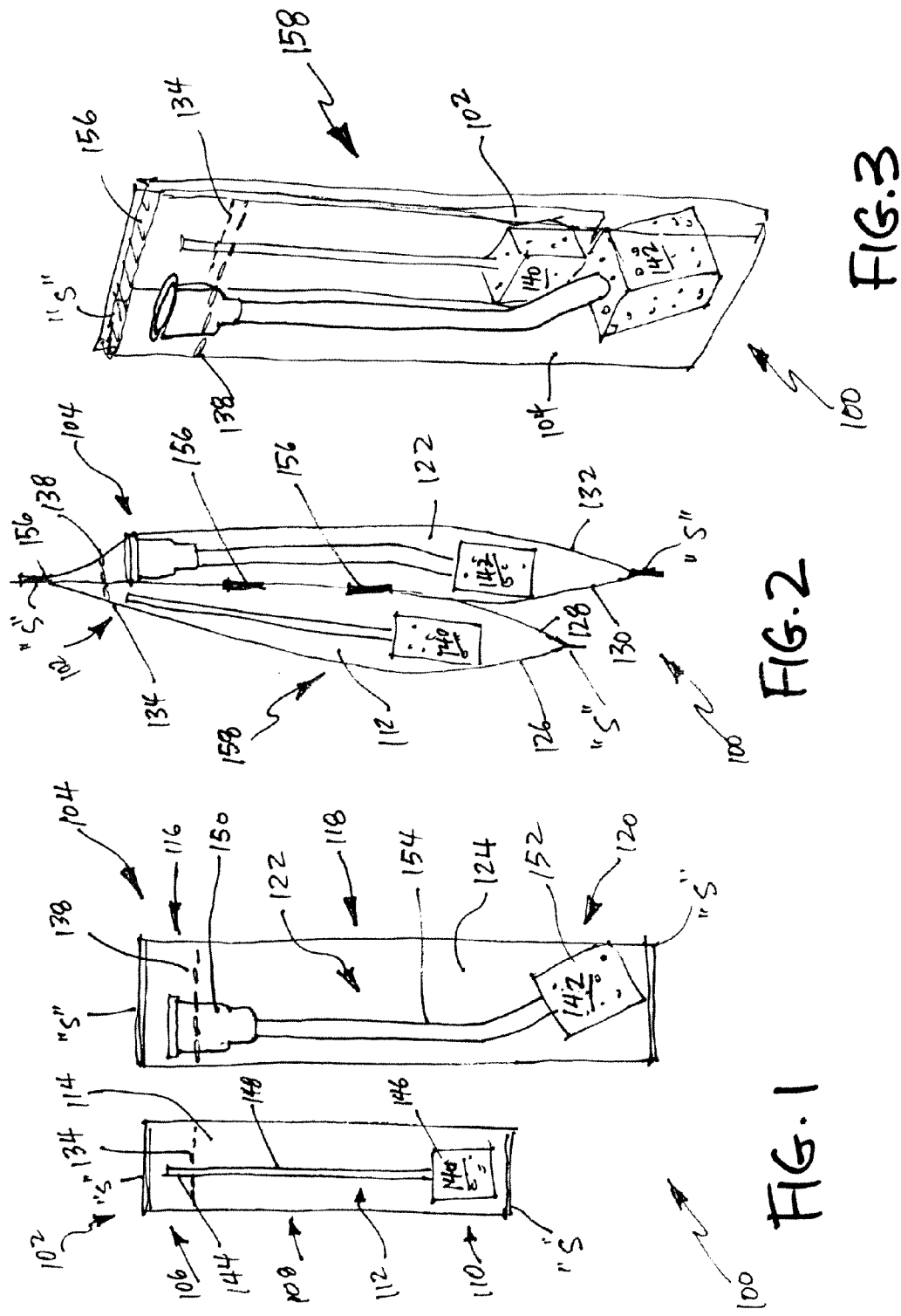

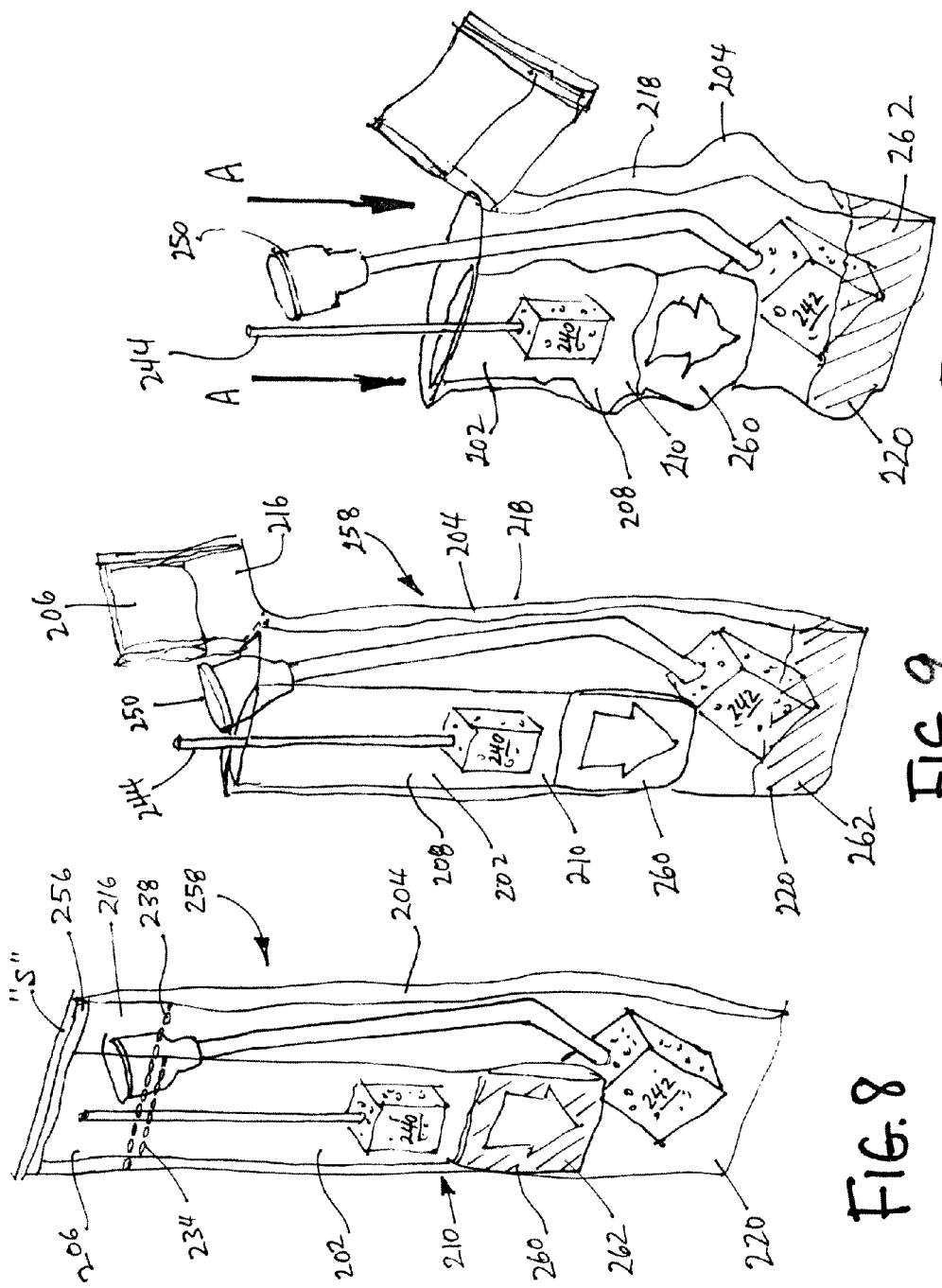

PACK OF ORAL CARE ITEMS

FIELD OF THE INVENTION

The present invention relates to oral care devices for cleaning the mouth of a patient having a temporary or permanent disability interfering with the patient's ability to practice oral hygiene.

BACKGROUND

There are many situations in which an individual is temporarily or permanently unable to practice oral hygiene in a convenient manner. One particular problem is presented by critical care patients in hospitals, as well as those in hospitals and nursing homes who require respirators to breath. Not only can the patient typically not walk or otherwise move to a restroom, the patient is often unable to hold the tooth brush and other oral hygiene instruments which are commonly used to keep one's mouth clean.

Because of these problems, the oral hygiene of many patients must be conducted by nurses or nurse's aides. The oral hygiene for each such patient must be worked in to an already hectic routine so convenience and ease of use is important.

Oral hygiene typically involves use of oral swabs, oral care applications and/or suctioning devices. Oral care swabs are typically designed for single use. Exemplary oral care swabs and oral care suction swabs are available from many companies including Kimberly-Clark Global Sales, Inc. of Roswell, Ga. Such swabs are typically impregnated with an oral care solution before treatment of a patient. For example, swabs have been dipped in various containers of oral care solutions before being used for oral care. In other examples, a burst pouch is incorporated within a sealed bag containing one or more swabs so that the swabs can be impregnated, while still in their package, before use to eliminate the step of dipping the swab in the container of oral care solution. See, for example, U.S. Pat. No. 5,378,226 for a "Swab Impregnating and Dispensing System" issued to Hanifl et al.

While such a package for impregnating swabs with oral care solution had advantages, different swabs are typically used to apply a mouth moisturizer and separate container or kits have been supplied for that purpose.

One attempt to address this problem is found in, for example, U.S. Pat. No. 5,709,866 for a "Dual Bag Mouth Care Package" issued to Booras et al., which teaches two sealed bags or pouches arranged in series to provide swab impregnating solution and a separate pouch of mouth moisturizing solution. That is, the two bags are arranged from end-to-end and are generally designed to be arranged in a horizontal position when opened. A first sealed bag contains a pair of oral care suction swabs and a burst pouch of swab impregnating solution. The first sealed bag is accessed through a first perforation line that is spaced from the side edges of the bag. A second sealed bag contains a sealed pouch that holds only a mouth moisturizing solution is applied to oral care suction swabs in the first bag. The contents of the second sealed bag are accessed through a second perforation line or through an end seal that is formed to allow the second bag to be opened at the end seal.

One disadvantage of such an arrangement is that all the swabs are in a single package (i.e., in the first sealed bag) which results in the entire contents (i.e., all the swabs) becoming impregnated with liquid when the burst pouch is fractured. Another disadvantage is the dispensing configuration of the package. A perforation line that is spaced from the side edges of the bag requires two hands to open or fracture the perforation line and two hands to manipulate the contents to and through the opening to dispense the contents. Moreover, the serial arrangement of the first bag and second bag results in each bag being opened sequentially in a separate action.

Accordingly, there is an unmet need for a pack of oral care items that provides simple and easy dispensing access to two or more individual items. In addition, there is an unmet need for a pack of oral care items that can be opened quickly, reliably and easily to access to items in separate packages. There is also a need for a pack of oral care items that allows for selective impregnation or saturation of some items but not others while providing simple and easy dispensing access to each item. Moreover, there is a need for a pack of oral care items that allows for selective impregnation or saturation of some items but not others while providing quick, simple and reliable access to items in separate packages.

SUMMARY OF THE INVENTION

In response to the difficulties and problems discussed herein, the present invention provides a pack of oral care items that allows for simultaneous opening and easy access to the items contained in the pack. The pack of oral care items includes two or more flexible packages. The flexible packages may be arranged in parallel (e.g., side-by-side). According to an aspect of the invention, one flexible package may be an inner package that is located substantially within another flexible package that forms an outer package.

Each flexible package has a top portion, a central portion, a bottom portion, an interior space, and an exterior surface. Each flexible package may optionally include a front side and an opposing back side. Each flexible package includes a frangible region located at or adjacent the top portion. The frangible region may be a series of perforations, a score line or weakened portion of the flexible package, a tear strip or the like.

At least one oral care item is disposed within the interior space of each flexible package. The flexible packages desirably correspond substantially to the size and geometry of the items contained therein. Desirably, each oral care item has a body that defines a top, a bottom and center. The top of each oral care item should be oriented to the corresponding top portion of each flexible package. That is, the end of the oral care item that would first be grasped by a user should be oriented to the portion of the flexible package that is opened. The oral care items may be selected from oral care applicator swabs, oral care suction swabs, denta swabs, suction toothbrushes, oropharangeal catheters or yankauer catheters. Desirably, each package contains an item having a different size or a different function. For example, one package may contain an oral care applicator swab and the other package may contain an oral care suction swab At least one fastening means joins the flexible packages together into a substantially unitary pack so the frangible regions are juxtaposed and the top portions of the packages are aligned. Such a configuration of the frangible regions and the top portions of the flexible packages allow for opening simultaneously by applying a force to the frangible regions to open the flexible packages and, optionally, removing the top portions of the flexible packages. Upon opening of the top portions of the flexible packages, the central portions of the flexible packages are configured for axial movement simultaneously toward the bottom portions to expose at least the tops of the oral care items so they can be readily grasped by a user.

At least a region of each flexible package is desirably transparent or at least translucent. While it is desirable that a substantial portion of the package is transparent so the contents of the package may be seen, selective portions of the package may be transparent to allow contents, indicia, markings or the like to be viewed.

According to an aspect of the invention, one or more of the flexible packages may optionally incorporate a burst pouch containing a liquid for release into the interior space of at least one of the flexible packages. According to another aspect of the invention, in a configuration where one flexible package may be an inner package that is located substantially within another flexible package that forms an outer package, one or both of the flexible packages may incorporate a burst pouch. Desirably, the inner package may include an integral burst pouch configured to release a liquid into the interior space of the outer package while keeping the interior space of the inner package dry. The liquid contained in the burst pouch may be any conventional oral care liquid including, but not limited to, an oral care cleaning solution, an anti-plaque solution, an oral debridement solution, a mouthwash, a moisturizer, a dentifrice, toothpaste or tooth cleaning solution, and combinations of the above.

The burst pouch may include indicia and/or instructions and at least a portion of the flexible packages may desirably be substantially transparent to allow visualization of the indicia and/or instructions. For example, the burst pouch of the inner package may include indicia and/or instructions and at least a portion of the outer package may be substantially transparent allowing visualization of the indicia and/or instructions.

The present invention encompasses a pack of oral care items that includes a flexible, outer package defining an interior space and a flexible inner package contained substantially within the outer package and in which the inner package defines an interior space. The inner package further including a burst pouch integrated with the inner package. The burst pouch contains a liquid and is configured to release the liquid into the interior space of the outer package while keeping the interior space of the inner package dry.

At least one oral care item is disposed within the interior space of each package. The inner and outer packages desirably correspond substantially to the size and geometry of the items contained therein. A frangible region is disposed on each package. The frangible regions are configured to create an opening to in interior space of each package.

At least one fastening means joins the flexible packages together into a substantially unitary pack so the frangible regions are juxtaposed and the top portions of the packages are aligned. Such a configuration of the frangible regions and top portions of the flexible packages allow for opening simultaneously by applying a force to the frangible regions to open the flexible packages and, optionally, removing the top portions of the flexible packages. Upon opening of the top portions of the flexible packages, the central portions of the flexible packages are configured for axial movement simultaneously toward the bottom portions to expose at least the tops of the oral care items so they can be readily grasped by a user.

Definitions

As used herein the following terms have the specified meanings, unless the context demands a different meaning or a different meaning is expressed; also, the singular generally includes the plural, and the plural generally includes the singular unless otherwise indicated.

As used herein, the terms "comprise," "comprises," "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the terms "align," "aligned," and/or "alignment" refers to the spatial property possessed by an arrangement or position of things in a straight line.

As used herein, the terms "orientation" or "position" used interchangeably herein refer to the spatial property of a place where something is situated or a way in which something is situated; for example, "the position of the hands on the clock."

As used herein, the term "about" adjacent to a stated number refers to an amount that is plus or minus ten (10) percent of the stated number.

These terms may be defined with additional language in the remaining portions of the specification.

BRIEF DESCRIPTION OF THE DRAWINGS

The above and other objects, features and advantages of the invention will become apparent from a consideration of the following detailed description presented in connection with the accompanying drawings in which:

FIG. 1 is an illustration showing a front view of flexible packages from an exemplary pack of oral care items;

FIG. 2 is an illustration showing a side view of an exemplary pack of oral care items;

FIG. 3 is an illustration showing a perspective view of an exemplary pack of oral care items;

FIG. 8 is an illustration showing a perspective view of a detail of an exemplary pack of oral care items;

FIG. 9 is an illustration showing a perspective view of a detail of an exemplary pack of oral care items; and FIG. 10 is an illustration showing a perspective view of a detail of an exemplary pack of oral care items.

DETAILED DESCRIPTION

Figures 4, 5:
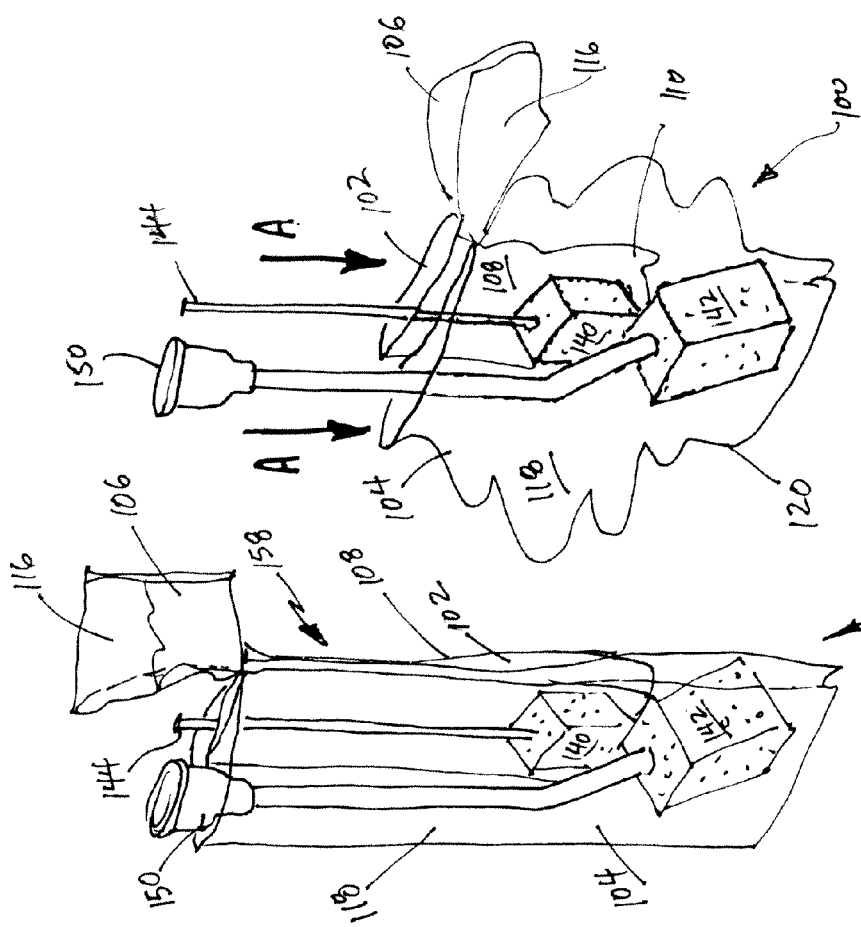
FIG. 4 is an illustration showing a perspective view of a detail of an exemplary pack of oral care items.
FIG. 5 is an illustration showing a perspective view of a detail of an exemplary pack of oral care items.

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Referring now to FIG. 1, there is shown an illustration of the components of a pack of oral care items 100 that allows for simultaneous opening and easy access to the items contained in the pack. The pack of oral care items 100 includes a first flexible package 102 and a second flexible package 104, although more than two flexible packages are contemplated. The flexible packages may be arranged in parallel (e.g., side-by-side) as generally illustrated in FIGS. 2 through 5. Alternatively and/or additionally, the flexible packages may be arranged in a different parallel configuration in which two or more of the packages are nested one within another as generally illustrated in FIGS. 6 and 8-10.

The first flexible package 102 has a top portion 106, a central portion 108, a bottom portion 110, an interior space 112, and an exterior surface 114. The second flexible package 104 has a top portion 116, a central portion 118, a bottom portion 120, an interior space 122, and an exterior surface 124. Each flexible package may optionally include a front side and an opposing back side. For example, the first flexible package 102 may have a front side 126 and an opposing back side 128 and the second flexible package 104 may have a front side 130 and an opposing back side 132. Each flexible package includes a frangible region located at or adjacent the top portion. For example, the first flexible package 102 may have a frangible region 134 located at or adjacent the top portion 106 and the second flexible package 104 may have a frangible region 138 located at or adjacent the top portion 116. The frangible region may be a series of perforations, a score line or weakened portion of the flexible package, a tear strip or the like or combinations of the same. The ends of the packages may be heat sealed or joined together by conventional techniques where such seals may be needed. For example, the bottom and top ends may be sealed with conventional heat seals "S" or other conventional sealing techniques. If one or more side seals are needed, the one or more sides may be sealed with conventional heat seals or other conventional sealing techniques.

At least one oral care item is disposed within the interior space of each flexible package. The oral care item may be disposed within the flexible package after the package is constructed except for one or more seals. It is also contemplated that the flexible package may be formed around the oral care item such as by sandwiching the oral care item between two sheets of material and creating the flexible package by sealing the ends of the sheets together. The oral care items may be selected from oral care applicator swabs, oral care suction swabs, denta swabs, suction toothbrushes, oropharangeal catheters or yankauer catheters. Desirably, each package contains an item having a different size or a different function. The flexible packages desirably correspond substantially to the size and geometry of the items contained therein.

For example, the first flexible package 102 may have an oral care applicator swab 140 and the second flexible package 104 may have an oral care suction swab 142. The oral care applicator swab 140 has a body that defines a top 144, a bottom 146 and center 148. The top 144 of the oral care applicator swab 140 should desirably be oriented to the corresponding top portion 106 of the first flexible package 102. That is, the end of the oral care applicator swab that a user will grasp to extract it from the package should be oriented to the portion of the flexible package that will be opened. The oral care suction swab 142 has a body that defines a top 150, a bottom 152 and center 154. The top 150 of the oral care suction swab 142 should be oriented to the corresponding top portion 116 of the second flexible package 104. That is, the end of the oral care suction swab that a user will grasp to extract it from the package should be oriented to the portion of the flexible package that will be opened.

At least one fastening means 156 joins the flexible packages 102 and 104 together into a substantially unitary pack 158 so the frangible regions 134 and 138 are juxtaposed and the top portions 106 and 116 of the packages are aligned. The fastening means 156 may be located at the top portions 106 and 116 above the frangible regions 134 and 138 and/or the fastening means may be in other locations such as, for example, the central portions 108 and 118. The fastening means 156 may be in the form of heat sealing the top ends or top portions 106 and 116 of the flexible packages 102 and 104 together. Alternatively and/or additionally, the fastening means 156 may be in the form of joining the sides and/or central portions 108 and 118 of the flexible packages 102 and 104 together using techniques such as, for example, heat sealing, heat bonding, thermally welding, adhesively bonding, adhesively tacking, taping or the like. For example, it is contemplated that an adhesive label or sticker may be used either alone or in combination with other techniques to join one or more portions of the flexible packages.

Referring now to FIG. 4, the configuration in which the frangible regions 134 and 138 are juxtaposed and the top portions 106 and 116 of the packages are aligned allow for opening simultaneously by applying a force (e.g., a tearing force, shear force, pulling force or the like) to the frangible regions to open the flexible packages and, optionally, removing the top portions of the flexible packages. It may be desirable to completely remove the top portions of the flexible packages. In that case, the frangible regions should extend completely across each package from side to side or from top to side to create a completely removable piece. It may also be desirable to have the top portions of the flexible packages remain attached upon opening. In that case, the frangible regions may extend only partially across each package to create an overlapping or juxtaposed section of packages lacking a frangible region so that applying a force separates the top portions of the packages at the frangible regions but not at the section of the packages lacking a frangible region.

Referring now to FIG. 5, upon opening of the top portions 106 and 116 of the flexible packages, the central portions 108 and 118 of the flexible packages 102 and 104 are configured for axial movement (along the direction of the arrows "A") simultaneously toward the bottom portions 110 and 120 to expose at least the tops 144 and 150 of the oral care items so they can be readily grasped by a user. For ease of illustration, the flexible packages 102 and 104 in all the figures (i.e., FIGS. 1-10) are shown as transparent. It is contemplated that portions, sections or regions of one or both of the flexible packages may be opaque and/or translucent. Desirably, at least a region of each flexible package is transparent or at least translucent to allow visualization of the contents, indicia, markings or the like.

Figure 6:
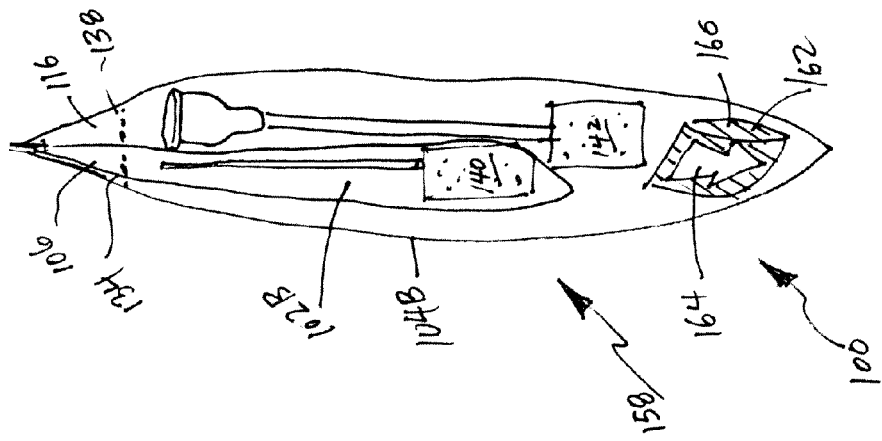
FIG. 6 is an illustration showing a side view of an aspect of an exemplary pack of oral care items.

Referring now to FIG. 6, which is a side view illustration, one or more of the flexible packages 102 and 104 may optionally incorporate a burst pouch 160 containing a liquid 162 for release into the interior space of at least one of the flexible packages. For example, the second flexible package 104 may include a burst pouch 160 and the first flexible package 102 may lack such a burst pouch. Alternatively, both the flexible packages 102 and 104 may include a burst pouch 160. FIG. 6 illustrates a side view showing a configuration in which the first flexible packages 102 is nested or contained within the second flexible package 104. That is, the first flexible package 102 may be an inner package 102B that is located substantially within the second flexible package 104 that forms an outer package 104B. In this configuration, the frangible regions 134 and 138 are juxtaposed and the top portions 106 and 116 of the packages are aligned allow for opening simultaneously by applying a force (e.g., a tearing force, shear force, pulling force or the like) to the frangible regions to open the flexible packages and, optionally, removing the top portions of the flexible packages. The burst pouch 160 may include indicia 164 and/or instructions and at least a portion of the flexible packages 102B and 104B may desirably be substantially transparent to allow visualization of the indicia 164 and/or instructions. For example, the burst pouch 160 of the outer package 104B may include indicia 164 and/or instructions about how to burst or fracture the burst pouch 160 and release the liquid 162 and at least a portion of the outer package 104B may be substantially transparent allowing visualization of the indicia 164 and/or instructions. The liquid 162 contained in the burst pouch 160 may be any conventional oral care liquid including, but not limited to, an oral care cleaning solution, an anti-plaque solution, an oral debridement solution, a mouthwash, a moisturizer, a dentifrice, toothpaste or tooth cleaning solution, and combinations of the above.

As generally illustrated in FIG. 6, an aspect of the present invention encompasses a pack of oral care items that includes a flexible, outer package defining an interior space and a flexible inner package contained substantially within the outer package and in which the inner package defines an interior space. According to an aspect of the invention, the inner package may further include a burst pouch integrated with the inner package. According to yet another aspect of the invention, the burst pouch contains a liquid and is configured to release the liquid into the interior space of the outer package while keeping the interior space of the inner package dry.

Figure 7:
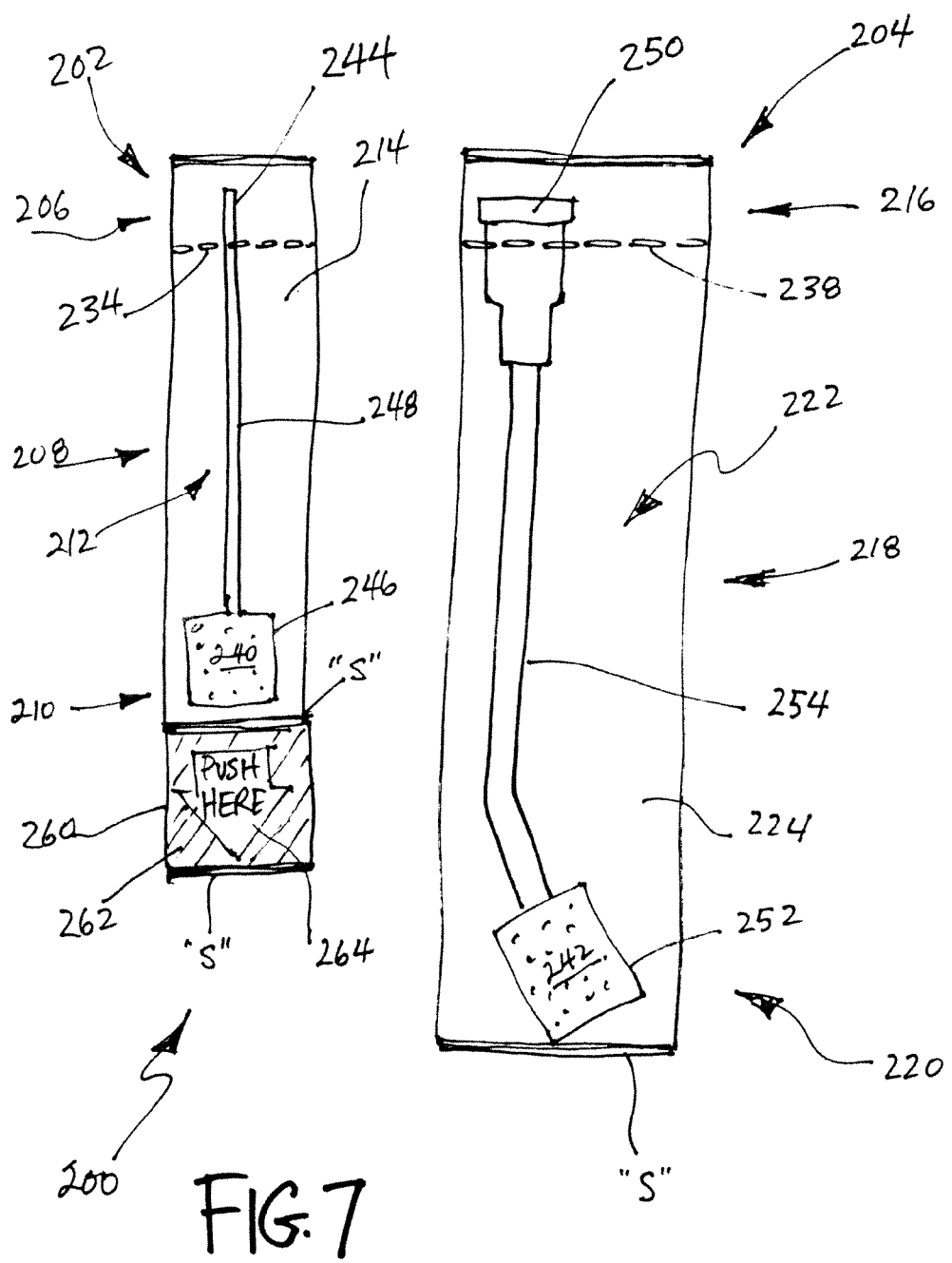
FIG. 7 is an illustration showing a front view of flexible packages from an exemplary pack of oral care items.

Referring now to FIG. 7, there is shown an illustration of the components of a pack of oral care items 200 that allows for simultaneous opening and easy access to the items contained in the pack and that includes a flexible inner package 202 that is contained within a flexible, outer package 204, although more than two flexible packages are contemplated. For example, more than one inner package may be contained within the outer package. Alternatively and/or additionally, an inner package may be contained within an outer package and that outer package may be joined to a second outer package (or even more outer packages) as generally illustrated in FIGS. 2-5. It is contemplated that the second outer package (or even more outer packages) may optionally include one or more inner packages.

The inner flexible package 202 has a top portion 206, a central portion 208, a bottom portion 210, an interior space 212, and an exterior surface 214. The inner flexible package 202 also includes a burst pouch 260 integrated with the inner flexible package. The burst pouch 260 contains a liquid 262 and may optionally include indicia and/or instructions 264 for activating or fracturing the burst pouch to release liquid. The burst pouch may be integrated with the inner package by joining a separately formed burst pouch to the inner package by conventional bonding or joining techniques. Alternatively and/or additionally, the burst pouch may be formed as a part of the inner package during manufacture of the inner package. For example, the inner package may be formed as a tubular blank that is sealed at the sides and the bottom. The blank may be filled with a predetermined amount of liquid and sealed again with a stronger, more robust seal at the fill line of the liquid. When pressure is applied to activate the burst pouch, the liquid preferentially ruptures the seal at the bottom of the pouch and not the stronger, more robust seal to prevent liquid from entering the interior of the inner pouch. Other manufacturing and assembly techniques are contemplated and would be available to those of ordinary skill in the art.

The outer flexible package 204 has a top portion 216, a central portion 218, a bottom portion 220, an interior space 222, and an exterior surface 224. Each flexible package may optionally include a front side and an opposing back side. Each flexible package includes a frangible region located at or adjacent the top portion. For example, the inner flexible package 202 may have a frangible region 234 located at or adjacent the top portion 206 and the outer flexible package 204 may have a frangible region 238 located at or adjacent the top portion 216.

As noted above, the frangible region may be a series of perforations, a score line or weakened portion of the flexible package, a tear strip or the like or combinations of the same. The ends of the packages may be heat sealed or joined together by conventional techniques where such seals may be needed. For example, the bottom and top ends and/or sides may be sealed with conventional heat seals "S" or other conventional sealing techniques.

At least one oral care item is disposed within the interior space of each flexible package as generally described above. The oral care items may be selected from oral care applicator swabs, oral care suction swabs, denta swabs, suction toothbrushes, oropharangeal catheters or yankauer catheters. Desirably, each package contains an item having a different size or a different function. The flexible packages desirably correspond substantially to the size and geometry of the items contained therein.

For example, the inner flexible package 202 may have an oral care applicator swab 240 and the outer flexible package 204 may have an oral care suction swab 242. The oral care applicator swab 240 has a body that defines a top 244, a bottom 246 and center 248. The top 244 of the oral care applicator swab 240 should desirably be oriented to the corresponding top portion 206 of the inner flexible package 202. That is, the end of the oral care applicator swab that a user will grasp to extract it from the package should be oriented to the portion of the flexible package that will be opened. The oral care suction swab 242 has a body that defines a top 250, a bottom 252 and center 254. The top 250 of the oral care suction swab 242 should be oriented to the corresponding top portion 216 of the outer flexible package 204. That is, the end of the oral care suction swab that a user will grasp to extract it from the package should be oriented to the portion of the flexible package that will be opened.

Referring to FIG. 8, at least one fastening means 256 joins the nested flexible inner package 202 and outer package 204 together into a substantially unitary pack 258 so the frangible regions 234 and 238 are juxtaposed and the top portions 206 and 216 of the packages are aligned. The fastening means 256 is desirably located at the top portions 206 and 216 above the frangible regions 234 and 238 and/or the fastening means may be in other locations such as, for example, the central portions 208 and 218. The fastening means may be in the form of heat sealing the top ends or top portions of the flexible packages together above the frangible regions 234 and 238. Alternatively and/or additionally, the fastening means may be in the form of joining the sides and/or central portions and/or other portions of the flexible packages together using techniques described above including adhesives, adhesive labels, thermal sealing and the like.

The configuration in which the frangible regions 234 and 238 are juxtaposed and the top portions 206 and 216 of the packages are aligned allows for opening simultaneously by applying a force (e.g., a tearing force, shear force, pulling force or the like) to the frangible regions to open the flexible packages and, optionally, removing the top portions of the flexible packages. The bust pouch 260 is activated by applying pressure or force to fracture or rupture the burst pouch to release liquid 262 which flows to the bottom 220 of the outer package 204 to impregnate or saturate the bottom 252 of the oral care suction swab 242 while keeping the liquid 262 away from the interior space 212 of the inner package 202 as well as its contents (e.g., the oral care applicator swab 240) as generally illustrated in FIG. 9. This is desirably done prior to opening the flexible packages.

Referring FIGS. 9 and 10, upon opening of the top portions 206 and 216 of the flexible packages, the central portions 208 and 218 of the flexible packages 202 and 204 are configured for axial movement (along the direction of the arrows "A") simultaneously toward the bottom portions 210 and 220 to expose at least the tops 244 and 250 of the oral care items so they can be readily grasped by a user.

Accordingly, the present invention provides a pack of oral care items that affords simple and easy dispensing access to two or more individual items. As can be seen, the flexible packages joined into a unitary article can be readily grasped by one hand allowing the other hand to open the top portions simultaneously and then move the central portions of the flexible packages axially toward the bottom portions of the packages to allow easy and unfettered one-handed dispensing of the contents. In addition, the present invention provides a pack of oral care items that can be opened quickly, reliably and easily to access to items in separate packages as well as allows for selective impregnation or saturation of some items but not others while providing simple and easy dispensing access to each item. Moreover, there is a need for a pack of oral care items that allows for selective impregnation or saturation of some items but not others while providing quick, simple and reliable access to items in separate packages. Those skilled in the art will appreciate numerous modifications which can be made without departing from the scope and spirit of the present invention. The appended claims are intended to cover such modifications and their functional equivalents.

What is claimed is:

1. A pack of oral care items comprising:
   two or more flexible packages, each flexible package having a top portion, a central portion, a bottom portion, an interior space, an exterior surface, a frangible region adjacent the top portion, and at least a region of each flexible package being transparent, one flexible package being an inner package located substantially within another flexible package that forms an outer package, wherein inner package includes an integral burst pouch configured to release a liquid into the interior space of the outer package while keeping the interior space of the inner package dry;
   at least one oral care item disposed within the interior space of each flexible package, each oral care item having a body defining top, a bottom and center, the top of each oral care item being oriented to the corresponding top portion of each flexible package; and
   at least one fastening means joining the flexible packages together into a substantially unitary pack so the frangible regions are juxtaposed and the top portions of the packages are aligned;
   wherein the top portions of the flexible packages are configured for opening simultaneously by applying a force to the frangible regions and, upon opening of the top portions, the central portions of the flexible packages are configured for axial movement simultaneously toward the bottom portions to expose at least the tops of the oral care items.

2. The pack of claim 1, wherein the flexible packages substantially correspond to the size and geometry of the items contained therein.

3. The pack of claim 1, wherein one package contains an oral care applicator swab and the other package contains an oral care suction swab.

4. The pack of claim 1, wherein the burst pouch of the inner package includes indicia and the outer package is substantially transparent allowing visualization of the indicia.

5. The pack of claim 1, wherein the liquid contained in the burst pouch is selected from an oral care cleaning solution, an anti-plaque solution, an oral debridement solution, a mouthwash, a moisturizer, a dentifrice, toothpaste or tooth cleaning solution, and combinations of the above.

6. The pack of claim 1, wherein each oral care item has a different size or a different function.

7. The pack of claim 1, wherein the frangible region is a region containing perforations.

8. A pack of oral care items comprising:
   a flexible outer package having a top portion, a central portion, a bottom portion, an interior space, an exterior surface, a frangible region adjacent the top portion, and at least a region of the flexible outer package being transparent;
   a flexible inner package contained within the outer package, the inner package having a top portion, a central portion, a bottom portion, an interior space, an exterior surface, a frangible region adjacent the top portion, and at least a region of the flexible inner package being transparent;
   a burst pouch containing a liquid for release into the interior space of at least one of the flexible packages, wherein the burst pouch is integrated with the inner package and configured to release the liquid into the interior space of the outer package while keeping the interior space of the inner package dry;
   at least one oral care item disposed within the interior space of each flexible package, each oral care item having a body defining top, a bottom and center, the top of each oral care item being oriented to the corresponding top portion of each flexible package; and
   at least one fastening means joining the flexible packages together into a substantially unitary pack so the frangible regions are juxtaposed and the top portions of the packages are aligned;
   wherein the top portions of the flexible packages are configured for opening simultaneously and, upon opening of the top portions, the central portions of the flexible packages are configured for axial movement simultaneously toward the bottom portions to expose at least the tops of the oral care items.

9. The pack of claim 8, wherein the inner and outer packages substantially correspond to the size and geometry of the items contained therein.

10. The pack of claim 8, wherein the inner package contains an oral care applicator swab and the outer package contains an oral care suction swab.

11. The pack of claim 8, wherein the burst pouch of the inner package includes indicia and the outer package is substantially transparent allowing visualization of the indicia.

12. The pack of claim 8, wherein the liquid contained in the burst pouch is selected from an oral care cleaning solution, an anti-plaque solution, an oral debridement solution, a mouthwash, a moisturizer, a dentifrice, toothpaste or tooth cleaning solution, and combinations of the above.

13. A pack of oral care items comprising:
- a flexible, outer package defining an interior space;
- a flexible inner package contained within the outer package, the inner package defining an interior space, the inner package further including a burst pouch integrated with the inner package, the burst pouch containing a liquid and configured to release the liquid into the interior space of the outer package while keeping the interior space of the inner package dry;
- at least one oral care item disposed within the interior space of each package, the inner and outer packages substantially corresponding to the size and geometry of the items contained therein;
- frangible regions disposed on each package, the frangible regions configured to create an opening to in interior space of each package;
- at least one fastening means joining the flexible packages together into a substantially unitary pack so the frangible regions are juxtaposed;
- wherein the packages are configured to be opened simultaneously by applying a force to the frangible regions and, upon opening, the central portions of the flexible packages are configured for axial movement simultaneously toward the bottom portions to expose at least the tops of the oral care items.

14. The pack of claim 13, wherein the inner package contains an oral care applicator swab and the outer package contains an oral care suction swab.

15. The pack of claim 13, wherein the burst pouch of the inner package includes indicia and the outer package is substantially transparent allowing visualization of the indicia.

16. The pack of claim 13, wherein the liquid contained in the burst pouch is selected from an oral care cleaning solution, an anti-plaque solution, an oral debridement solution, or a mouthwash.

* * * * *